(12) United States Patent
O'Brien et al.

(10) Patent No.: US 6,624,177 B1
(45) Date of Patent: *Sep. 23, 2003

(54) MATRIX METALLOPROTEINASE INHIBITORS AND THEIR THERAPEUTIC USES

(75) Inventors: Patrick Michael O'Brien, Stockbridge; Joseph Armand Picard, Canton; Drago Robert Sliskovic, Saline; Andrew David White, Pinckney, all of MI (US)

(73) Assignee: Warner-Lambert Company, Morris Plains, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 132 days.

(21) Appl. No.: 09/254,384

(22) PCT Filed: Aug. 22, 1997

(86) PCT No.: PCT/US97/14859
§ 371 (c)(1),
(2), (4) Date: Mar. 2, 1999

(87) PCT Pub. No.: WO98/09934
PCT Pub. Date: Mar. 12, 1998

Related U.S. Application Data
(60) Provisional application No. 60/025,062, filed on Sep. 4, 1996.

(51) Int. Cl.[7] ............... C07D 209/82; C07D 333/78; C07D 307/91; A61K 31/195; A61D 9/10
(52) U.S. Cl. ............... 514/326; 514/4; 514/468; 546/196; 548/569; 549/454; 549/461
(58) Field of Search ............... 549/460, 461; 514/468, 414, 326, 422; 548/454, 565; 546/196

(56) References Cited

U.S. PATENT DOCUMENTS

| | | | | |
|---|---|---|---|---|
| 3,845,097 | A | 10/1974 | Toyoshima et al. | 260/471 |
| 4,097,472 | A | 6/1978 | Okamoto et al. | 424/177 |
| 5,627,206 | A | 5/1997 | Hupe et al. | 514/468 |
| 5,665,764 | A * | 9/1997 | Hupe et al. | 514/468 |
| 6,207,698 | B1 * | 3/2001 | Wantanabe et al. | 514/414 |

FOREIGN PATENT DOCUMENTS

| | | |
|---|---|---|
| DE | 20 65 966 | 7/1977 |
| EP | 183271 | * 6/1986 |
| EP | 0 183 271 | 5/1990 |
| EP | 0 606 046 | 7/1994 |
| JP | 0 183 271 | * 11/1985 |
| WO | 96 38434 | 12/1996 |
| WO | 97 19068 | 5/1997 |
| WO | 97 27174 | 7/1997 |

OTHER PUBLICATIONS

Polman, C.H. et al, BMJ 2000, 321, 490–4.*
Cohen, J.A. et al, J. Neuroimmun., 1999, 98 29–36.*
"Cecil Textbook of Medicine, 20th Edition", Bennett, J.C. Editor, W.B. Saunders, Philadelphia, 1996, pp. LVIII–LIX.*
"Merck Manual of Diagnosis and Therapy, 16th Edition", Berkow, R. Editor–in–Chief, Merck Research Laboratories, Rahway, N.J., 1992, pp. 2792–2793.*
Skiles, J.W.. et al, Annual Reports in Medical Chemistry, vol. 35, Academic Press, San Diego, 2000 pp. 167–176.*
Abdel–Ghaffar, et al., *J. Serb. Chem. Soc.,* Synthesis of Biologically Active Fluorene–2–Sulphonylamino Acid and Dipeptide Derivatives, vol. 55, No. 6, 1990, pp. 311–317.
El–Nagger et al., *Acta Pharm. Jugosl.,* Synthesis and Biological Activity of Some New Dibenzofuran–and 7–Nitrodibenzofuran–2–Sulphonylamino Acid Derivatives, V–35, 1985, pp 15–22.
PCT International Search Report, PCT/US97/14859.

* cited by examiner

*Primary Examiner*—Mukund J. Shah
*Assistant Examiner*—Thomas McKenzie
(74) *Attorney, Agent, or Firm*—Andrew J. Leon; Todd M. Crissey

(57) ABSTRACT

The present invention relates to a method of inhibiting matrix metalloproteinases using compounds that are dibenzofuran sulfonamide derivatives having the Formula I

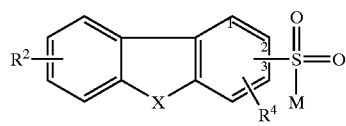

More particularly, the present invention relates to a method of treating diseases in which matrix melatoproteinases are involved such as multiple sclerosis, atherosclerotic plaque rupture, restenosis, aortic aneurism, heart failure, periodontal disease, corneal ulceration, burns, decubital ulcers, chronic ulcers or wounds, cancer metastasis, tumor angiogenesis, arthritis, or other autoimmune or inflammatory diseases dependent upon tissue invasion by leukocytes.

15 Claims, No Drawings

MATRIX METALLOPROTEINASE INHIBITORS AND THEIR THERAPEUTIC USES

This application claims the benefit of Provisional application Ser. No. 60/025,062, filed Sep. 4, 1996.

FIELD OF THE INVENTION

The present invention relates to a method of inhibiting matrix metalloproteinases using compounds that are dibenzofuran sulfonamide derivatives. More particularly, the present invention relates to a method of treating diseases in which matrix metalloproteinases are involved such as multiple sclerosis, atherosclerotic plaque rupture, restenosis, aortic aneurism, heart failure, periodontal disease, corneal ulceration, burns, decubital ulcers, chronic ulcers or wounds, cancer metastasis, tumor angiogenesis, arthritis, or other autoimmune or inflammatory diseases dependent upon tissue invasion by leukocytes.

BACKGROUND OF THE INVENTION

The compounds of the present invention are inhibitors of matrix metalloproteinases, e.g., stromelysin-1 and gelatinase A (72 kDa gelatinase).

Stromelysin-1 and gelatinase A are members of the matrix metalloproteinases (MMP). Other members include fibroblast collagenase, neutrophil collagenase, gelatinase B (92 kDa gelatinase), stromelysin-2, stromelysin-3, matrilysin, collagenase 3, and the newly discovered membrane-associated matrix metalloproteinases (Sato H., Takino T., Okada Y., Cao J., Shinagawa A., Yamamoto E., and Seiki M., *Nature*, 1994;370:61–65).

Stromelysin-1 is also known as MMP03 and gelatinase A is known as MMP02. In addition, several other matrix metalloproteinases are known:

MMP01—Fibroblast collagenase;
MMP07—Matrilysin;
MMP09 Gelatinase B; and
MMP13—Collagenase -3.

The catalytic zinc in matrix metalloproteinases is typically the focal point for inhibitor design. The modification of substrates by introducing chelating groups has generated potent inhibitors such as peptidehydroxamates and thiol-containing peptides. Peptide hydroxamates and the natural endogenous inhibitors of MMPs (TIMPs) have been used successfully to treat animal models of cancer and inflammation.

The ability of the matrix metalloproteinases to degrade various components of connective tissue makes them potential targets for controlling pathological processes. For example, the rupture of atherosclerotic plaques is the most common event initiating coronary thrombosis. Destabilization and degradation of the extracellular matrix surrounding these plaques by MMPs has been proposed as a cause of plaque fissuring. The shoulders and regions of foam cell accumulation in human atherosclerotic plaques show locally increased expression of gelatinase B, stromelysin-1, and interstitial collagenase. In situ zymography of this tissue revealed increased gelatinolytic and caseinolytic activity (Galla Z. S., Sukhova G. K., Lark M. W., and Libby P., "Increased expression of matrix metalloproteinases and matrix degrading activity in vulnerable regions of human atherosclerotic plaques", *J. Clin. Invest.*, 1994;94:2494–2503). In addition, high levels of stromelysin RNA message have been found to be localized to individual cells in atherosclerotic plaques removed from heart transplant patients at the time of surgery (Henney A. M., Wakeley P. R., Davies M. J., Foster K., Hembry R., Murphy G., and Humphries S., "Localization of stromelysin gene expression in atherosclerotic plaques by in situ hybridization," *Proc. Nat'l. Acad. Sci.*, 1991;88:8154–8158).

Inhibitors of matrix metalloproteinases will have utility in treating degenerative aortic disease associated with thinning of the medial aortic wall. Increased levels of the proteolytic activities of MMPs have been identified in patients with aortic aneurisms and aortic stenosis (Vine N. and Powell J. T., "Metalloproteinases in degenerative aortic diseases," *Clin. Sci.*, 1991;81:233–239).

Heart failure arises from a variety of diverse etiologies, but a common characteristic is cardiac dilation which has been identified as an independent risk factor for mortality (Lee T. H., Hamilton M. A., Stevenson L. W., Moriguchi J. D., Fonarow G. C., Child J. S., Laks H., and Walden J. A., "Impact of left ventricular size on the survival in advanced heart failure," *Am. J. Cardiol.*, 1993;72:672–676). This remodeling of the failing heart appears to involve the breakdown of extracellular matrix. Matrix metalloproteinases are increased in patients with both idiopathic and ischemic heart failure (Reddy H. K., Tyagi S. C., Tjaha I. E., Voelker D. J., Campbell S. E., and Weber K. T., "Activated myocardial collagenase in idiopathic dilated cardiomyopathy," *Clin. Res.*, 1993;41:660A; Tyagi S. C., Reddy H. K., Voelker D., Tjara I. E., and Weber K. T., "Myocardial collagenase in failing human heart," *Clin. Res.*, 1993;41:681A). Animal models of heart failure have shown that the induction of gelatinase is important in cardiac dilation (Armstrong P. W., Moe G. W., Howard R. J., Grima E. A., and Cruz T. F., "Structural remodeling in heart failure: gelatinase induction," *Can. J. Cardiol.*, 1994;10:214–220), and cardiac dilation precedes profound deficits in cardiac function (Sabbah H. N., Kono T., Stein P. D., Mancini G. B., and Goldstein S., "Left ventricular shape changes during the course of evolving heart failure," *Am. J. Physiol.*, 1992;263:H266–H270). Neointimal proliferation, leading to restenosis, frequently develops after coronary angioplasty. The migration of vascular smooth muscle cells (VSMCs) from the tunica media to the neointima is a key event in the development and progression of many vascular diseases and a highly predictable consequence of mechanical injury to the blood vessel (Bendeck M. P., Zempo N., Clowes A. W., Galardy R. E., and Reidy M., "Smooth muscle cell migration and matrix metalloproteinase expression after arterial injury in the rat," *Circulation Research*, 1994;75:539–545). Northern blotting and zymographic analyses indicated that gelatinase A was the principal MMP expressed and excreted by these cells. Further, antisera capable of selectively neutralizing gelatinase A activity also inhibited VSMC migration across basement membrane barrier. After injury to the vessel, gelatinase A activity increased more than 20-fold as VSCMs underwent the transition from a quiescent state to a proliferating, motile phenotype (Pauly R. R., Passaniti A., Bilato C., Monticone R., Cheng L., Papadopoulos N., Gluzband Y. A., Smith L., Weinstein C., Lakatta E., and Crow M. T., "Migration of cultured vascular smooth muscle cells through a basement membrane barrier requires type IV collagenase activity and is inhibited by cellular differentiation," *Circulation Research*, 1994;75:41–54).

Collagenase and stromelysin activities have been demonstrated in fibroblasts isolated from inflamed gingiva (Uitto V. J., Applegren R., and Robinson P. J., "Collagenase and neutral metalloproteinase activity in extracts from inflamed human gingiva," *J. Periodontal Res.*, 1981;16:417–424), and enzyme levels have been correlated to the severity of gum disease (Overall C. M., Wiebkin O. W., and Thonard J. C., "Demonstrations of tissue collagenase activity in vivo and its relationship to inflammation severity in human gingiva," *J. Periodontal Res.*, 1987;22:81–88). Proteolytic degradation of extracellular matrix has been observed in corneal ulceration following alkali burns (Brown S. I., Weller C. A., and Wasserman H. E., "Collagenolytic activity of alkali burned corneas," *Arch. Opthalmol.*, 1969;81:370–373). Thiol-containing peptides inhibit the collagenase isolated from alkali-burned rabbit corneas (Burns F. R., Stack M. S., Gray R. D., and Paterson C. A., *Invest. Opththamol.*, 1989;30:1569–1575).

Stromelysin is produced by basal keratinocytes in a variety of chronic ulcers (Saarialho-Kere U. K., Ulpu K., Pentland A. P., Birkedal-Hansen H., Parks W. C., Welgus H. G., "Distinct populations of basal keratinocytes express stromelysin-1 and stromelysin-2 in chronic wounds," *J. Clin. Invest.*, 1994;94:79–88).

Stromelysin-1 mRNA and protein were detected in basal keratinocytes adjacent to but distal from the wound edge in what probably represents the sites of proliferating epidermis. Stromelysin-1 may thus prevent the epidermis from healing. Davies, et al., (*Cancer Res.*, 1993;53:2087–2091) reported that a peptide hydroxamate, BB-94, decreased the tumor burden and prolonged the survival of mice bearing human ovarian carcinoma xenografts. A peptide of the conserved MMP propeptide sequence was a weak inhibitor of gelatinase A and inhibited human tumor cell invasion through a layer of reconstituted basement membrane (Melchiori A., Albili A., Ray J. M., and Stetler-Stevenson W. G., *Cancer Res.*, 1992;52:2353–2356), and the natural tissue inhibitor of metalloproteinase-2 (TIMP-2) also showed blockage of tumor cell invasion in in vitro models (DeClerck Y. A., Perez N., Shimada H., Boone T. C., Langley K. E., and Taylor S. M., *Cancer Res.*, 1992;52:701–708). Studies of human cancers have shown that gelatinase A is activated on the invasive tumor cell surface (Strongin A. Y., Marmer B. L., Grant G. A., and Goldberg G. I., *J. Biol Chem.*, 1993;268:14033–14039) and is retained there through interaction with a receptor-like molecule (Monsky W. L., Kelly T., Lin C.-Y., Yeh Y., Stetler-Stevenson W. G., Mueller S. C., and Chen W.-T., *Cancer Res.*, 1993;53:3159–3164). Inhibitors of MMPs have shown activity in models of tumor angiogenesis (Taraboletti G., Garofalo A., Belotti D., Drudis T., Borsotti P., Scanziani E., Brown P. D., and Giavazzi R., *Journal of the National Cancer Institute*, 1995;87:293; and Benelli R., Adatia R., Ensoli B., Stetler-Stevenson W. G., Santi L., and Albini A., *Oncolog Research*, 1994;6:251–257).

Several investigators have demonstrated consistent elevation of stromelysin and collagenase in synovial fluids from rheumatoid and osteoarthritis patients as compared to controls (Walakovits L. A., Moore V. L., Bhardwaj N., Gallick G. S., and Lark M. W., "Detection of stromelysin and collagenase in synovial fluid from patients with rheumatoid arthritis and post-traumatic knee injury," *Arthritis Rheum.*, 1992;35:35–42; Zafarullah M., Pelletier J. P., Cloutier J. M., and Marcel-Pelletier J., "Elevated metalloproteinases and tissue inhibitor of metalloproteinase mRNA in human osteoarthritic synovia," *J. Rheumatol.*, 1993;20:693–697). TIMP-1 and TIMP-2 prevented the formation of collagen fragments, but not proteoglycan fragments, from the degradation of both the bovine nasal and pig articular cartilage models for arthritis, while a synthetic peptide hydroxamate could prevent the formation of both fragments (Andrews H. J., Plumpton T. A., Harper G. P., and Cawston T. E., *Agents Actions*, 1992;37:147–154; Ellis A. J., Curry V. A., Powell E. K., and Cawston T. E., *Biochem. Biophys. Res. Commun.*, 1994;201:94–101).

Gijbels, et al., (*J. Clin. Invest.*, 1994;94:2177–2182) recently described a peptide hydroxamate, GM6001, that suppressed the development or reversed the clinical expression of experimental allergic encephalomyelitis (EAE) in a dose dependent manner, suggesting the use of MMP inhibitors in the treatment of autoimmune inflammatory disorders such as multiple sclerosis. A recent study by Madri has elucidated the role of gelatinase A in the extravasation of T-cells from the blood stream during inflammation (Ramnanic A. M. and Madri J. A., "The Induction of 72-kD Gelatinase in T Cells upon Adhesion to Endothelial Cells is VCAM-1 Dependent," *J. Cell Biology*, 1994; 125:1165–1178). This transmigration past the endothelial cell layer is coordinated with the induction of gelatinase A and is mediated by binding to the vascular cell adhesion molecule-1 (VCAM-1). Once the barrier is compromised, edema and inflammation are produced in the CNS. Leukocytic migration across the blood-brain barrier is known to be associated with the inflammatory response in EAE. Inhibition of the metalloproteinase gelatinase A would block the degradation of extracellular matrix by activated T-cells that is necessary for CNS penetration.

These studies provided the basis for the belief that an inhibitor of stromelysin-1 and/or gelatinase A will treat diseases involving disruption of extracellular matrix resulting in inflammation due to lymphocytic infiltration, inappropriate migration of metastatic or activated cells, or loss of structural integrity necessary for organ function.

We have identified a series of tricyclic aromatic sulfonamide compounds that are inhibitors of matrix metalloproteinases, particularly stromelysin-1 and gelatinase A, and thus useful as agents for the treatment of multiple sclerosis, atherosclerotic plaque rupture, restenosis, aortic aneurism, heart failure, periodontal disease, corneal ulceration, burns, decubital ulcers, chronic ulcers or wounds, cancer metastasis, tumor angiogenesis, arthritis, or other autoimmune or inflammatory diseases dependent upon tissue invasion by leukocytes.

SUMMARY OF THE INVENTION

The present invention provides a method of inhibiting a matrix metalloproteinase in a patient in need of matrix metalloproteinase inhibition comprising administering to the patient a therapeutically effective amount of a compound of Formula I

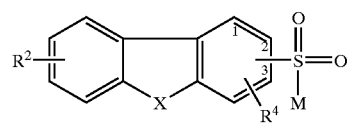

wherein M is a natural (L) alpha amino acid derivative having the structure

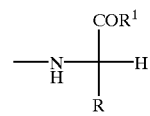

X is O, S, S(O)$_n$, CH$_2$, CO, or NR$^Q$;

R$^Q$ is hydrogen, C$_1$–C$_6$ alkyl, or —C$_1$–C$_6$ alkyl-phenyl;

R is a side chain of a natural alpha amino acid;

$R^1$ is $C_1$–$C_5$ alkoxy, hydroxy, or —$NHOR^5$;

$R^2$ and $R^4$ are independently hydrogen, —$C_1$–$C_5$ alkyl, phenyl —$NO_2$, halogen, —$OR^5$, —CN, —$CO_2R^5$, —$SO_3R^5$, —CHO, —$COR^5$, —$CONR^5R^6$, —$(CH_2)_nNR^5R^6$, —$CF_3$, or —$NHCOR^5$;

each $R^5$ and $R^6$ are independently hydrogen or $C_1$–$C_5$ alkyl; and n is 0 to 2, and the pharmaceutically acceptable salts, esters, amides and prodrugs thereof.

In one embodiment of the invention of Formula I, X is O.

In another embodiment of the invention of Formula I, X is S.

In another embodiment of the invention of Formula I, X is $CH_2$.

In another embodiment of the invention of Formula I, X is $NR^Q$.

In a preferred embodiment of the invention of Formula I, X is O and $R^2$ and $R^4$ are hydrogen.

In another embodiment of the invention of Formula I, X is CO.

In another embodiment of the invention of Formula I, X is $S(O)_n$.

In another preferred embodiment of the invention of Formula I, $R^1$ is hydroxy, $C_1$–$C_5$ alkoxy, —NHOH, or —NHObenzyl.

In still another preferred embodiment, R is the side chain of the natural alpha amino acid glycine, alanine, valine, leucine, isoleucine, cysteine, aspartic acid, or phenylalanine.

In another embodiment, the present invention provides a method of inhibiting a matrix metalloproteinase in a patient in need of matrix metalloproteinase inhibition, the method comprising administering to the patient a therapeutically effective amount of a compound of Formula II

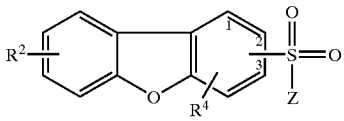

II wherein Z is a natural (L) amino acid derivative having the structure

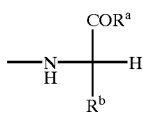

$R^2$ and $R^4$ are independently hydrogen, —$C_1$–$C_5$ alkyl, phenyl —$NO_2$, halogen, —$OR^5$, —CN, —$CO_2R^5$, —$SO_3R^5$, —CHO, —$COR^5$, —$CONR^5R^6$, —$(CH_2)_nNR^5R^6$, —$CF_3$, or —$NHCOR^5$;

each $R^5$ and $R^6$ are independently hydrogen or $C_1$–$C_5$ alkyl;

$R^a$ is $C_1$–$C_5$ alkoxy, hydroxy, or —$NHOR^c$;

$R^b$ is a side chain of a natural alpha amino acid; and $R^c$ is hydrogen, $C_1$–$C_5$ alkyl, or —$CH_2$ phenyl; and n is 0 to 2, and the pharmaceutically acceptable salts, esters, amides, and prodrugs thereof.

In a preferred embodiment of the method comprising Formula II, the group

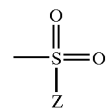

is located at the 2-position of the phenyl ring.

In another preferred embodiment of the method comprising Formula II, the

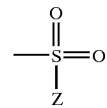

is located at the 3-position of the phenyl ring.

Also provided is a method of inhibiting a matrix metalloproteinase in a patient in need of matrix metalloproteinase inhibition, the method comprising administering to the patient a therapeutically effective amount of a compound of Formula III

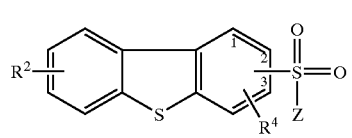

III wherein Z is a natural (L) amino acid derivative having the structure

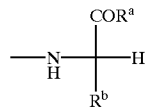

$R^2$ and $R^4$ are independently hydrogen, —$C_1$–$C_5$ alkyl, phenyl —$NO_2$, halogen, —$OR^5$, —CN, —$CO_2R^5$, —$SO_3R^5$, —CHO, —$COR^5$, —$CONR^5R^6$, —$(CH_2)_nNR^5R^6$, —$CF_3$, or —$NHCOR^5$;

each $R^5$ and $R^6$ are independently hydrogen or $C_1$–$C_5$ alkyl;

$R^a$ is $C_1$–$C_5$ alkoxy, hydroxy, or —$NHOR^c$;

$R^b$ is a side chain of a natural alpha amino acid; and $R^c$ is hydrogen, $C_1$–$C_5$ alkyl, or —$CH_2$ phenyl; and n is 0 to 2, and the pharmaceutically acceptable salts, esters, amides, and prodrugs thereof.

Also provided is a method of inhibiting a matrix metalloproteinase in a patient in need of matrix metalloproteinase inhibition, the method comprising administering to the patient a therapeutically effective amount of a compound of Formula IV.

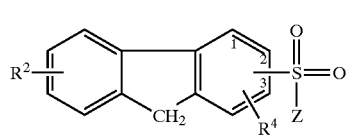

IV wherein Z is a natural (L) amino acid derivative having the structure

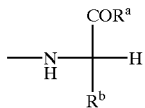

R² and R⁴ are independently hydrogen, —C₁–C₅ alkyl, phenyl —NO₂, halogen, —OR⁵, —CN, —CO₂R⁵, —SO₃R⁵, —CHO, —COR⁵, —CONR⁵R⁶, —(CH₂)ₙNR⁵R⁶, —CF₃, or —NHCOR⁵;

each R⁵ and R⁶ are independently hydrogen or C₁–C₅ alkyl;

Rᵃ is C₁–C₅ alkoxy, hydroxy, or —NHORᶜ;

Rᵇ is a side chain of a natural alpha amino acid; and Rᶜ is hydrogen, C₁–C₅ alkyl, or —CH₂ phenyl; and n is 0 to 2, and the pharmaceutically acceptable salts, esters, amides, and prodrugs thereof.

Also provided is a method of inhibiting a matrix metalloproteinase in a patient in need of matrix metalloproteinase inhibition, the method comprising administering to the patient a therapeutically effective amount of a compound of Formula V

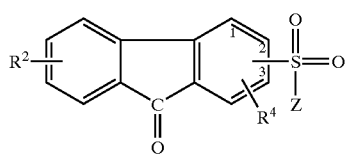
V wherein Z is a natural (L) amino acid derivative having the structure

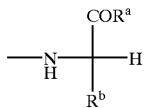

R² and R⁴ are independently hydrogen, —C₁–C₅ alkyl, phenyl —NO₂, halogen, —OR⁵, —CN, —CO₂R⁵, —S₃R⁵, —CHO, —COR⁵, —CONR⁵R⁶, —(CH₂)ₙNR⁵R⁶, —CF₃, or —NHCOR⁵;

each R⁵ and R⁶ are independently hydrogen or C₁–C₅ alkyl;

Rᵃ is C₁–C₅ alkoxy, hydroxy, or —NHORᶜ;

Rᵇ is a side chain of a natural alpha amino acid; and Rᶜ is hydrogen, C₁–C₅ alkyl, or —CH₂ phenyl; and n is 0 to 2, and the pharmaceutically acceptable salts, esters, amides, and prodrugs thereof.

Also provided is a method of inhibiting a matrix metalloproteinase in a patient in need of matrix metalloproteinase inhibition, the method comprising administering to the patient a therapeutically effective amount of a compound of Formula VI

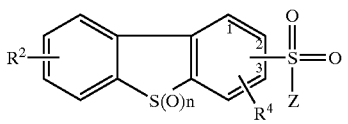
VI wherein Z is a natural (L) amino acid derivative having the structure

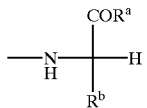

R² and R⁴ are independently hydrogen, —C₁–C₅ alkyl, phenyl —NO₂, halogen, —OR⁵, —CN, —CO₂R⁵, —SO₃R⁵, —CHO, —COR⁵, —CONR⁵R⁶, —(CH₂)ₙNR⁵R⁶, —CF₃, or —NHCOR⁵;

each R⁵ and R⁶ are independently hydrogen or C₁–C₅ alkyl;

Rᵃ is C₁–C₅ alkoxy, hydroxy, or —NHORᶜ;

n is 0 to 2;

Rᵇ is a side chain of a natural alpha amino acid; and Rᶜ is hydrogen, C₁–C₅ alkyl, or —CH₂ phenyl; and n is 0 to 2, and the pharmaceutically acceptable salts, esters, amides, and prodrugs thereof.

Also provided is a method of inhibiting a matrix metalloproteinase in a patient in need of matrix metalloproteinase inhibition, the method comprising administering to the patient a therapeutically effective amount of a compound of Formula VII

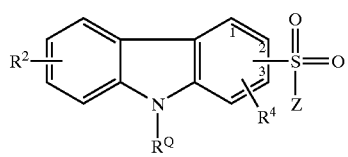
VII wherein Z is a natural (L) amino acid derivative having the structure

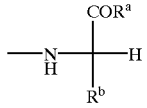

R² and R⁴ are independently hydrogen, —C₁–C₅ alkyl, phenyl —NO₂, halogen, —OR⁵, —CN, —CO₂R⁵, —SO₃R⁵, —CHO, —COR⁵, —CONR⁵R⁶, —(CH₂)ₙNR⁵R⁶, —CF₃, or —NHCOR⁵;

each R⁵ and R⁶ are independently hydrogen or C₁–C₅ alkyl;

Rᵃ is C₁–C₅ alkoxy, hydroxy, or —NHORᶜ;

R^Q is hydrogen, C₁–C₆ alkyl, or C₁–C₆ alkyl-phenyl;

Rᵇ is a side chain of a natural alpha amino acid; and Rᶜ is hydrogen, C₁–C₅ alkyl, or —CH₂ phenyl; and n is 0 to 2, and the pharmaceutically acceptable salts, esters, amides, and prodrugs thereof.

In a most preferred embodiment, the compound of Formula I–VIII is:

(L)-2-(dibenzofuran-2-sulfonylamino)-4-methyl-pentanoic acid;

(L)-2-(dibenzofuran-2-sulfonylamino)-3-methyl-pentanoic acid;

(L)-2-(dibenzofuran-2-sulfonylamino)-3-phenyl-propionic acid;

(L)-2-(dibenzofuran-2-sulfonylamino)-propionic acid;

(L)-2-(dibenzofuran-2-sulfonylamino)-3-methyl-butyric acid;

(L)-2-(dibenzofuran-2-sulfonylamino)-acetic acid;

(L)-2-(dibenzofuran-2-sulfonylamino)-succinic acid;
(L)-2-(dibenzofuran-2-sulfonylamino)-3-tritylsulfanyl-propionic acid;
(L)-2-(dibenzofuran-2-sulfonylamino)-3-mercapto-propionic acid;
(L)-2-(dibenzofuran-2-sulfonylamino)-3-methyl-pentanoic acid hydroxyamide;
(L)-2-(dibenzofuran-2-sulfonylamino)-acetic acid tert-butyl ester;
(L)-2-(dibenzofuran-2-sulfonylamino)-propionic acid tert-butyl ester;
(L)-2-(dibenzofuran-2-sulfonylamino)-propionic acid tert-butyl ester;
(L)-2-(dibenzofuran-2-sulfonylamino)-4-methyl-pentanoic acid tert-butyl ester;
(L)-2-(dibenzofuran-2-sulfonylamino)-3-methyl-pentanoic acid tert-butyl ester;
(L)-2-(dibenzofuran-2-sulfonylamino)-3-methyl-pentanoic acid benzyloxy-amide;
(L)-2-(dibenzofuran-2-sulfonylamino)-3-phenyl-propionic acid tert-butyl ester;
(L)-2-(dibenzofuran-3-sulfonylamino)-3-methyl-butyric acid;
3-Methyl-2-(9-methyl-9H-carbazole-3-sulfonylamino)-butyric acid;
2-(9-Benzyl-9H-carbazole-3 -sulfonylamino)-3-methyl-butyric acid;
(L)-2-(9H-Fluorene-2-sulfonylamino)-3-methyl-butyric acid;
(L)-2-(5,5-Dioxo-5H-5$\lambda^6$-dibenzothiophene-3-sulfonylamino)-3-methyl-butyric acid;
(L)-2-(Dibenzothiophene-2-sulfonylamino)-3-methyl-butyric acid;
(L)-2-(7-Bromo-dibenzofuran-2-sulfonylamino)-3-methyl-butyric acid;
(L)-3-Methyl-2-(7-phenyl dibenzofuran-2-sulfonylamino)-butyric acid; and
2-(9H-Carbazole-3-sulfonylamino)-3 -methyl-butyric acid.

Also provided by the present invention is a method of treating multiple sclerosis, the method comprising administering to a patient having multiple sclerosis a therapeutically effective amount of a compound of Formula I–VIII.

Also provided by the present invention is a method of treating atherosclerotic plaque rupture, the method comprising administering to a patient having an atherosclerotic plaque at risk for rupture a therapeutically effective amount of a compound of Formula I–VIII.

Also provided by the present invention is a method of treating or preventing restenosis, the method comprising administering to a patient having restenosis or at risk of having restenosis a therapeutically effective amount of a compound of Formula I–VIII.

Also provided by the present invention is a method of treating aortic aneurism, the method comprising administering to a patient having aortic aneurism a therapeutically effective amount of a compound of Formula I–VIII.

Also provided by the present invention is a method of treating heart failure, the method comprising administering to a patient having heart failure a therapeutically effective amount of a compound of Formula I–VIII.

Also provided by the present invention is a method of treating periodontal disease, the method comprising administering to a patient having periodontal disease a therapeutically effective amount of a compound of Formula I–VIII.

Also provided by the present invention is a method of treating corneal ulceration, the method comprising administering to a patient having corneal ulceration a therapeutically effective amount of a compound of Formula I–VIII.

Also provided by the present invention is a method of treating burns, the method comprising administering to a patient having burns a therapeutically effective amount of a compound of Formula I–VIII.

Also provided by the present invention is a method of treating decubital ulcers, the method comprising administering to a patient having decubital ulcers a therapeutically effective amount of a compound of Formula I–VIII.

Also provided by the present invention is a method of treating chronic ulcers or wounds, the method comprising administering to a patient having chronic ulcers or wounds a therapeutically effective amount of a compound of Formula I–VIII.

Also provided by the present invention is a method of treating cancer metastasis, the method comprising administering to a patient having cancer metastasis a therapeutically effective amount of a compound of Formula I–VIII.

Also provided by the present invention is a method of treating tumor angiogenesis, the method comprising administering to a patient having tumor angiogenesis a therapeutically effective amount of a compound of Formula I–VIII.

Also provided by the present invention is a method of treating arthritis, the method comprising administering to a patient having arthritis a therapeutically effective amount of a compound of Formula I–VIII.

Also provided by the present invention is a method of treating autoimmune or inflammatory diseases dependent upon tissue invasion by leukocytes, the method comprising administering to a patient having autoimmune or inflammatory diseases dependent upon tissue invasion by leukocytes a therapeutically effective amount of a compound of Formula I–VIII.

The present invention also provides compounds of Formula I

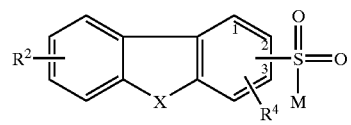

wherein M is a natural (L) alpha amino acid derivative having the structure

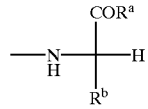

X is S, S(O)$_n$, CH$_2$, CO, or NR$^Q$;
R$^b$ is a side chain of a natural alpha amino acid;
R$^Q$ is hydrogen, C$_1$–C$_6$ alkyl, or —C$_1$–C$_6$ alkyl-phenyl;
R$^a$ is C$_1$–C$_5$ alkoxy, hydroxy, or —NHOR$^5$;
R$^2$ and R$^4$ are independently hydrogen, —C$_1$–C$_5$ alkyl, phenyl —NO$_2$, halogen, —OR$^5$, —CN, —CO$_2$R$^5$, —SO$_3$R$^5$, —CHO, —COR$^5$, —CONR$^5$R$^6$, —(CH$_2$)$_n$NR$^5$R$^6$, —CF$_3$, or —NHCOR$^5$;
each R$^5$ and R$^6$ are independently hydrogen or C$_1$–C$_5$ alkyl; and
n is 0 to 2, and the pharmaceutically acceptable salts, esters, amides, and prodrugs thereof.

The present invention also provides compounds of Formula VIII

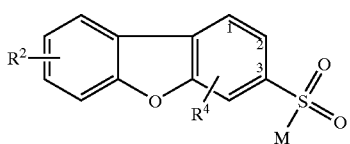

VIII wherein M is a natural (L) alpha amino acid derivative having the structure

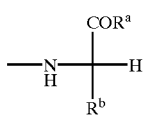

$R^2$ and $R^4$ are independently hydrogen, —$C_1$–$C_5$ alkyl, phenyl —$NO_2$, halogen, —$OR^5$, —CN, —$CO_2R^5$, —$SO_3R^5$, —CHO, —$COR^5$, —$CONR^5R^6$, —$(CH_2)_nNR^5R^6$, —$CF_3$, or —$NHCOR^5$;

$R^b$ is a side chain of a natural alpha amino acid;

$R^a$ is $C_1$–$C_5$ alkoxy, hydroxy, or —$NHOR^5$;

$R^2$ and $R^4$ are independently hydrogen, —$C_1$–$C_5$ alkyl, phenyl —$NO_2$, halogen, —$OR^5$, —CN, —$CO_2R^5$, —$SO_3R^5$, —CHO, —$COR^5$, —$CONR^5R^6$, —$(CH_2)_nNR^5R^6$, —$CF_3$, or —$NHCOR^5$;

each $R^5$ and $R^6$ are independently hydrogen or $C_1$–$C_5$ alkyl; and n is 0 to 2, and the pharmaceutically acceptable salts, esters, amides, and prodrugs thereof.

DETAILED DESCRIPTION OF THE INVENTION

The present invention provides a method of inhibiting a matrix metalloproteinase in a patient in need of matrix metalloproteinase inhibition comprising administering to the patient a therapeutically effective amount of a compound of Formula I

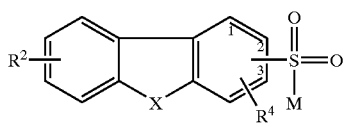

I wherein M is a natural (L) alpha amino acid derivative having the structure

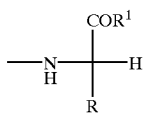

X is O, S, $S(O)_n$, $CH_2$, CO, or $NR^Q$;

R is a side chain of a natural alpha amino acid;

$R^1$ is $C_1$–$C_5$ alkoxy, hydroxy, or —$NHOR^5$;

$R^2$ and $R^4$ are independently hydrogen, —$C_1$–$C_5$ alkyl, phenyl —$NO_2$, halogen, —$OR^5$, —CN, —$CO_2R^5$, —$SO_3R^5$, —CHO, —$COR^5$, —$CONR^5R^6$, —$(CH_2)_nNR^5R^6$, —$CF_3$, or —$NHCOR^5$;

each $R^5$ and $R^6$ are independently hydrogen or $C_1$–$C_5$ alkyl; and n is 0 to 2, and the pharmaceutically acceptable salts, esters, amides, and prodrugs thereof.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "alkoxy" means an alkyl group attached to an oxygen atom. Representative examples of alkoxy groups include methoxy, ethoxy, tert-butoxy, propoxy, and isobutoxy.

The term "halogen" includes chlorine, fluorine, bromine, and iodine.

The term "phenyl" also includes substituted phenyl wherein one or more hydrogen on the phenyl ring is replaced with an organic radical. Examples of suitable substituents include, but are not limited to, halogen, $C_1$–$C_6$ alkoxy, —$CF_3$, —$NO_2$, —$NH_2$, —$NH(C_1$–$C_6$ alkyl), or —$N(C_1$–$C_6$ alkyl)$_2$.

The symbol "—" means a bond.

The term "side chain of a natural alpha amino acid" means the group Q in a natural amino acid of formula $H_2N$—CH (Q)—COOH. Examples of side chains of natural alpha amino acids include those of alanine, arginine, asparagine, aspartic acid, cysteine, glutamic acid, glycine, histidine, isoleucine, leucine, lysine, methionine, phenylalanine, proline, serine, threonine, tryptophan, tyrosine and valine.

A natural alpha amino acid is an amino acid found in a living organism. Examples of such amino acids include glycine, alanine, valine, leucine, isoleucine, phenylalanine, proline, serine, threonine, tyrosine, asparagine, glutamine, lysine, arginine, tryptophan, histidine, cysteine, methionine, aspartic acid, and glutamic acid.

The functional groups in the amino acid side chains can be protected. For example, carboxyl groups can be esterified, amino groups can be converted to amides or carbamates, hydroxyl groups can be converted to ethers or esters, and thiol groups can be converted to thioethers or thioesters.

The compounds of Formula I–VIII can be administered to a patient either alone or as part of a pharmaceutically acceptable composition. The compositions can be administered to patients such as humans and animals either orally, rectally, parenterally (intravenously, intramuscularly or subcutaneously), intracisternally, intravaginally, intraperitoneally, intravesically, locally (powders, ointments or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols, and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 1,000 mg per day. For a normal human adult having a body weight of about 70 kg, a dosage in the range of about 0.01 to about 100 mg/kg of body weight per day is preferable. The specific dosage used, however, can vary. For example, the dosage can depend on a numbers of factors including the requirements of the patient, the severity of the condition being treated, and the pharmacological activity of the compound being used. The determination of optimum dosages for a particular patient is well-known to those skilled in the art. The term "patient" includes humans and animal.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laureate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as nontoxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, S. M. Berge, et al., "Pharmaceutical Salts," *J. Pharm. Sci.*, 1977:66(1–19) which is incorporated herein by reference.)

Examples of pharmaceutically acceptable, nontoxic esters of the compounds of this invention include $C_1$ to $C_6$ alkyl esters wherein the alkyl group is a straight or branched chain. Acceptable esters also include $C_5$ to $C_7$ cycloalkyl esters as well as arylalkyl esters such as, but not limited to benzyl. $C_1$ to $C_4$ alkyl esters are preferred. Esters of the compounds of the present invention may be prepared according to conventional methods.

Examples of pharmaceutically acceptable, nontoxic amides of the compounds of this invention include amides derived from ammonia, primary $C_1$ to $C_6$ alkyl amines, and secondary $C_1$ to $C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$ to $C_3$ alkyl primary amines and $C_1$ to $C_2$ dialkyl secondary amines are preferred. Amides of the compounds of the invention may be prepared according to conventional methods.

The term "prodrug" refers to compounds that are rapidly transformed in vivo to yield the parent compound of the above formula, for example, by hydrolysis in blood. A thorough discussion is provided in T. Higuchi and V. Stella, "Pro-drugs as Novel Delivery Systems," Vol 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention are administered to a patient in need of matrix metalloproteinase inhibition. In general, patients in need of matrix metalloproteinase inhibition are those patients having a disease or condition in which a matrix metalloproteinase plays a role. Examples of such diseases include, but are not limited to, multiple sclerosis, atherosclerotic plaque rupture, restenosis, aortic aneurism, heart failure, periodontal disease, corneal ulceration, bums, decubital ulcers, chronic ulcers or wounds, cancer metastasis, tumor angiogenesis, arthritis, or other autoimmune or inflammatory diseases dependent upon tissue invasion by leukocytes.

In a preferred embodiment, the matrix metalloproteinase is stromelysin-1 or gelatinase-A.

A "therapeutically effective amount" is an amount of a compound of Formula I–VIII that when administered to a patient having a disease that can be treated with a compound of Formula I–VIII ameliorates a symptom of the disease. A therapeutically effective amount of a compound of Formula I–VIII is readily determined by one skilled in the art by administering a compound of Formula I–VIII to a patient and observing the results.

The following examples illustrate particular embodiments of the invention and are not intended to limit the scope of the specification, including the Claims, in any manner.

EXAMPLES

General Dibenzofuran Sulfonamide Synthesis

The compounds of the present invention can be synthesized using a number of different synthetic routes. Referring to the General Synthetic Scheme, the common starting materials are the sulfonyl chlorides (1). These are easily synthesized by one skilled in the art by sulfonation of the parent heterocycle. Some representative procedures are as follows. For dibenzofuran (1, X=O) and dibenzothiophene (1, X=S), the parent heterocycle is sulfonated at the 2-position using one equivalent of chlorosulfonic acid in chloroform at 0° C. according to the method of Bassin, et al., (Phosphorus, Sulfur and Silicon, 1992;72:157–170). The sulfonic acid is then converted to the corresponding sulfonyl chloride (1, X=O,S) by treatment with phosphorus pentachloride at 170–180° C. For carbazole (1, X=NH), the parent heterocycle is sulfonated at the 3-position using sulfuric acid at 100° C. followed by neutralization with barium carbonate to yield the barium salt of the corresponding sulfonic acid according to the method of Loza, et al., (Sb. Mater. Nauch.-Tekh. Konf. Ukrain. Zaoch. Poitekh. Inst. Vith, Kharkov, 1966:202–205). The sulfonic acid is then converted to the corresponding sulfonyl chloride (1, X=NH) by treatment with phosphorus pentachloride at 170–180° C. or reaction with either phosphoryl chloride, thionyl chloride, or oxalyl chloride. For fluorene (1, X=$CH_2$), according to the method of Chrzaszczewska et al., (Lodz. Tow. Nauk., Wydz. 3, Acta Chim., 1966;11:143–155) the parent carbocycle is sulfonated at the 2-position using one equivalent of chlorosulfonic acid in chloroform at 0° C. followed by neutralization with potassium hydroxide to give the potassium salt of the corresponding sulfonic acid. This fluorene derivative can then be oxidized using aqueous potassium permanganate at 80° C. to the corresponding fluorenone derivative (1, X=CO). The sulfonic acid salts are then converted to the corresponding sulfonyl chloride (1, X=$CH_2$,CO) by treatment with phosphorus pentachloride and phosphoryl chloride in chloroform.

In Method A, the sulfonyl chloride (1) is condensed directly with a natural amino acid using a base such as triethylamine (TEA) in a mixture of tetrahydrofuran (THF) and water (3:5) at 10° C. to yield the desired compound (2). The corresponding hydroxamic acid (5) can be conveniently prepared by coupling the acid (2) with an O-protected (usually benzyl) hydroxylamine using dicyclohexylcarbodiimide (DCC) as the coupling agent in dichloromethane at temperatures ranging from –(10) to 0° C. The protecting group can be removed from compound (4) by catalytic hydrogenolysis using hydrogen gas at 50 psi and Pd/$BaSO_4$ in aqueous methanol to yield the hydroxamic acid derivative (5).

In Method B, the sulfonyl chloride (1) is condensed with a suitably C-protected (usually tertiary butyl ester) amino acid using a base such as N-methylmorpholine (NMM) in a solvent such as dichloromethane at 0° C. to yield compound (3). The protecting group can be removed from the carboxylic acid by treatment with trifluoroacetic acid in dichloromethane at 25–35° C. using anisole as a carbocation scavenger to yield (2).

General Synthetic Scheme

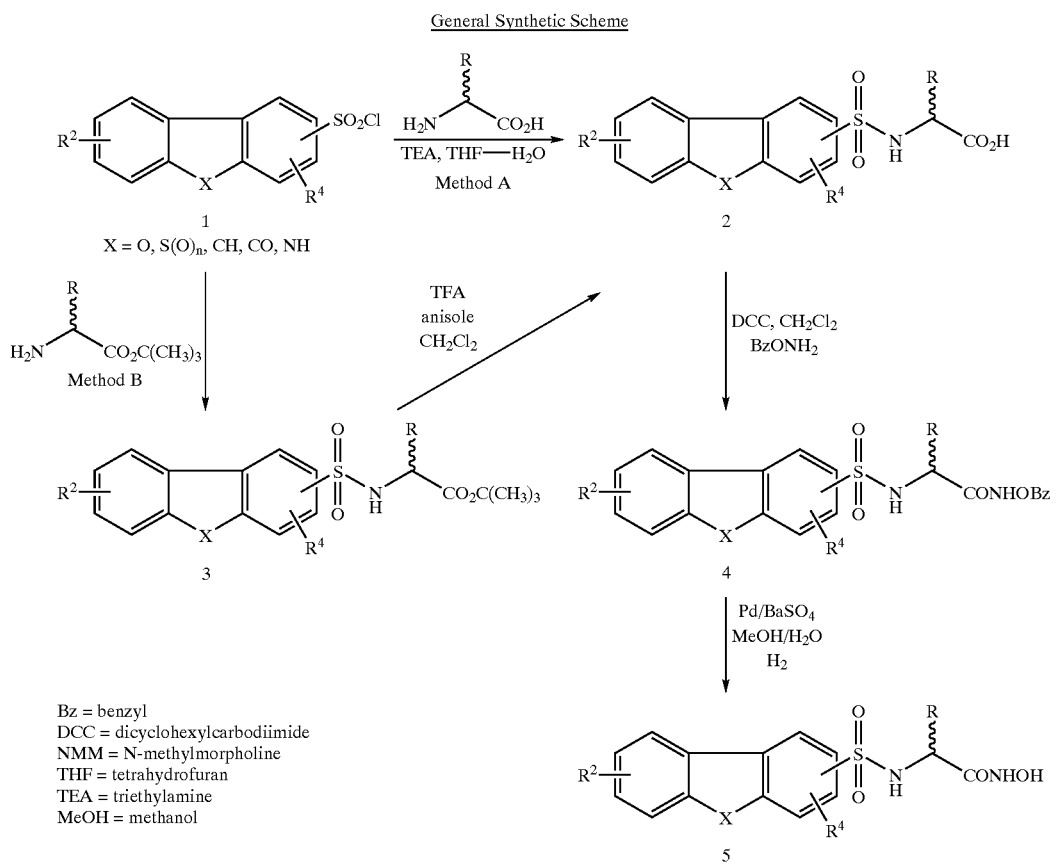

Bz = benzyl
DCC = dicyclohexylcarbodiimide
NMM = N-methylmorpholine
THF = tetrahydrofuran
TEA = triethylamine
MeOH = methanol

EXAMPLES PREPARED BY METHOD A

Example 1

(L)-2-(Dibenzofuran-2-sulfonylamino)-4-methyl-pentanoic Acid

Step (a) (L)-2-(Dibenzofuran-2-sulfonylamino)-4-methyl-pentanoic Acid, tert.-Butyl Ester To a dichloromethane solution (20 mL) of (L)-leucine, tert.-butyl ester (2.1 g, 0.0099 mol) and N-methylmorpholine (2.2 mL, 0.0199 mol) at 0° C. under an inert nitrogen atmosphere was added a dichloromethane solution (10 mL) of dibenzofuran-2-sulfonyl chloride (1.0 g, 0.00375 mol) with stirring. The resulting solution was stirred at 0° C. for 4 hours and then partitioned with water (30 mL). The organic layer was separated and washed with water (2×30 mL) and brine (2×30 mL). This was then dried over anhydrous magnesium sulfate, filtered, and the solvent removed under reduced pressure. The residue was then flash chromatographed on silica gel and the title product (1.0 g, 64%) was eluted with 20% ethyl acetate/hexane; melting point=106–109° C.

Step (b) (L)-2-(Dibenzofuran-2-sulfonylamino)-4-methyl-pentanoic Acid (Example 1)

To a dichloromethane solution (5 mL) of the material obtained in step (a) (0.5 g, 0.00119 mol) and anisole (0.5 mL) at room temperature with stirring was added trifluoroacetic acid (5 mL). The resulting solution was stirred at room temperature for 24 hours and then concentrated in vacuo. The residue was triturated with a mixture of ethyl acetate/hexane to yield the title compound (0.14 g, 33%); melting point=75–80° C.

$^1$H NMR (CDCl$_3$: δ 8.4 (s, 1H), 8.0 (d, 1H), 7.9 (d, 1H), 7.4–7.6 (m, 4H), 5.0 (d, 1H), 3.9 (m, 1H), 1.8 (m, 1H), 1.4 (m, 2H), 0.9 (d, 3H), 0.8 (d, 3H) ppm.

Following the general procedure of Example 1, the following compounds were obtained:

Example 2

(L)-2-(Dibenzofuran-2-sulfonylamino)-3-methyl-pentanoic Acid $^1$H NMR (DMSO-D$_6$): δ 8.6 (s, 1H), 8.3 (d, 1H), 8.1 (d, 1H), 7.8–7.9 (m, 3H), 7.6 (tr, 1H), 7.5 (tr, 1H), 3.7 (m, 1H), 3.4 (s, 1H), 1.7 (m, 1H), 1.1–1.4 (m, 2H), 0.75–0.85 (m, 6H) ppm.

Example 3

(L)-2-(Dibenzofuran-2-sulfonylamino)-3-phenyl-propionic Acid; Melting Point=196–198° C.

EXAMPLES PREPARED BY METHOD B

Example 4

(L)-2-(Dibenzofuran-2-sulfonylamino)-propionic Acid

To a THF/water (5:3, 8 mL) solution of (L)-alanine (0.3 g, 0.0034 mol) and triethylamine (1 mL) at 10° C. was added dibenzofuran-2-sulfonyl chloride (1.0 g, 0.00375 mol) in one portion with stirring. The resulting solution was stirred at room temperature for 24 hours. The solution was then concentrated in vacuo and the residue redissolved in water (10 mL). This solution was cooled in an ice bath and then acidified with 1N HCl. A white solid was deposited which was then filtered and washed with water. This solid was recrystallized from aqueous ethanol to give the title product (0.6 g, 50%); melting point=158–163° C.

Following the general procedure of Example 4, the following compounds were obtained:

Example 5

(L)-2-(Dibenzofuran-2-sulfonylamino)-3-methyl-butyric Acid; Melting Point=163–165° C.

Example 6

(Dibenzofuran-2-sulfonylamino)-acetic Acid; Melting Point=208–210° C.

Example 7

(L)-2-(Dibenzofuran-2-sulfonylamino)-succinic Acid; Melting Point=165–168° C.

Example 8

(L)-2-(Dibenzofuran-2-sulfonylamino)-3-tritylsulfanyl-propionic Acid $^1$NMR (DMSO-D$_6$): δ 8.5 (s, 1H), 8.2 (m, 2H), 7.1–7.9 (m, 19H), 3.6 (m, 1H), 3.5 (m, 1H), 2.3 (d, 2H) ppm.

Example 9

(L)-2-(Dibenzofuran-2-sulfonylamino)-3-mercapto-propionic Acid

To a dichloromethane solution (10 mL) of (L)-2-(Dibenzofuran-2-sulfonylamino)-3-tritylsulfanyl-propionic acid (Example 8, 1.0 g, 0.00168 mol) at room temperature was added trifluoroacetic acid (10 mL). A deep red/orange solution resulted. To this solution was added triethylsilane (0.33 mL, 0.00202 mol), the color was immediately discharged, and the resulting clear solution was stirred at room temperature for 3 hours. The solution was then concentrated in vacuo and the residue redissolved in ether (10 mL) which was then removed in vacuo. This procedure was repeated three times. The residue was recrystallized from ethyl acetate/hexane (1:1) to yield the title compound (0.23 g, 39%); melting point=164–166° C.

Example 10

(L)-2-(Dibenzofuran-2-sulfonylamino)-3-methyl-pentanoic acid hydroxyamide

Step (a) (L)-2-(Dibenzofuran-2-sulfonylamino)-3-methyl-pentanoic Acid Benzyloxy-amide To a THF solution (50 mL) of (L)-2-(Dibenzofuran-2-sulfonylamino)-3-methyl-pentanoic acid (Example 2, 0.55 g, 0.0015 mol) and carbonyldiimidazole (0.26 g, 0.0016 mol) at room temperature under an inert nitrogen atmosphere was added O-benzylhydroxylamine (0.23 g, 0.0018 mol) in one portion. This solution was then heated to reflux for 72 hours and then allowed to stir at room temperature for 24 hours. The mixture was then concentrated in vacuo and flash chromatographed on silica gel eluting with ethyl acetate/hexane (1:4) to yield the title compound (0.27 g, 38%); melting point=207–209° C.

Step (b) (L)-2-(Dibenzofuran-2-sulfonylamino)-3-methyl-pentanoic Acid Hydroxyamide (Example 10)

A THF (2 mL)/methanol (10 mL) solution of the material obtained above in step (a) (0.037 g, 0.0000793 mol) was hydrogenolyzed using hydrogen gas at 50 psi with a Pd/BaSO$_4$ catalyst at room temperature for 1 hour. The catalyst was removed by filtration and the solution concentrated in vacuo. The residue was triturated with ether to yield the title compound (0.022 g, 74%).

$^1$H NMR (CDCl$_3$): δ 8.6–7.2 (m, 8H), 5.1 (m, 1H), 4.1 (m, 1H), 1.9–1.2 (m, 3H), 0.9 (m, 3H), 0.85 (m, 3H) ppm.

Example 11

(L)-2-(dibenzofuran-3-sulfonylamino)-3-methyl-butyric Acid

Step (a) (Dibenzofuran-3-sulfonyl Chloride)

3-Aminodibenzofuran (10 g, 54.6 mol) was diazotized by dissolving in 180 mL glacial acetic acid, 50 mL water, and 14 mL concentrated hydrochloric acid at 0° C. and adding 15 mL of a 5.5 M aqueous solution of sodium nitrite. The resulting mixture was stirred for 1 hour before pouring into a solution of copper(II)chloride (2.0 g, 14.9 mmol) in 240 mL of a 1:1 mixture of benzene and glacial acetic acid saturated with sulfur dioxide. This mixture was allowed to warm to room temperature and stirred for 16 hours. The reaction was partitioned between water and chloroform. The chloroform layer was washed with water, dried over magnesium sulfate, filtered, and concentrated to give the title compound as a yellowish solid; melting point=142–144° C.

Step (b)

Using the procedure of Example 1, (L)-leucine, tert.-butyl ester is replaced with (L)-valine, tert.-butyl ester and dibenzofuran-2-sulfonyl chloride is replaced with dibenzofuran-3-sulfonyl chloride, the title compound is obtained; melting point=197–200° C.

Example 12

(L)-2-(9H-Fluorene-2-sulfonylamino)-3-methyl-butyric Acid

When in the procedure of Example 1, (L)-leucine, tert.-butyl ester is replaced with (L)-valine, tert.-butyl ester and dibenzofuran-2-sulfonyl chloride is replaced with 9H-fluorene-2-sulfonyl chloride, the title compound is obtained.

Example 13

(L)-2-(5,5-Dioxo-5H-5λ$^6$-dibenzothiophene-3-sulfonylamino)-3-methyl-butyric Acid When in the procedure of Example 1, (L)-leucine, tert.-butyl ester is replaced with (L)-valine, tert.-butyl ester and dibenzofuran-2-sulfonyl chloride is replaced with 5,5-dioxo-5H-5λ$^6$-dibenzothiophene-3-sulfonyl chloride, the title compound is obtained; melting point 85–90° C.

Example 14

(L)-2-(Dibenzothiophene-2-sulfonylamino)-3-methyl-butyric Acid

When in the procedure of Example 1, (L)-leucine, tert.-butyl ester is replaced with (L)-valine, tert.-butyl ester and dibenzofuran-2-sulfonyl chloride is replaced with dibenzothiophene-2-sulfonyl chloride, the title compound is obtained; melting point=150–155° C.

Example 15

(L)-2-(5,5-Dioxo-5H-5λ$^6$-dibenzothiophene-2-sulfonylamino)-3-methyl-butyric Acid To a glacial acetic acid (30 mL) solution of the material obtained in Example 14 Step (a) (1.5 g, 0.0036 mol) was added 10 mL of 30% hydrogen peroxide. The resulting solution was heated to reflux for 2.5 hours, cooled to room temperature and stirred for 16 hours and then filtered to give the crude product as a white solid. The solid was washed with water and boiling ether to yield the title compound; melting point=216–218° C.

Example 16

(L)-2-(7-Bromo-dibenzofuran-2-sulfonylamino)-3-methyl-butyric Acid

Step (a) 3-Bromo-dibenzofuran

3-Amino-dibenzofuran (15 g, 81.9 mmoles) was added in portions to a suspension of cupric bromide (21.9 g, 98.2 mmoles) and tert.-butyl nitrite (12.66 g, 122.8 mmoles) in 350 mL of acetonitrile. This mixture was heated to reflux for 2 hours and then stirred for 16 hours at room temperature. The reaction was partitioned between 1 M HCl and diethyl ether. The diethyl ether layer was washed with brine, dried over magnesium sulfate, filtered, and concentrated to give an oily solid. Chromatography gave the title compound as a yellowish solid.

Step (b) 7-Bromo-dibenzofuran-2-sulfonyl Chloride

Chlorosulfonic acid (3.75 mL, 56 mmoles) was added dropwise to a solution of 3-bromo-dibenzofuran (9.21 g, 37.3 mmoles) in 150 mL of chloroform at room temperature. The reaction was stirred for 5 hours, cooled to 0° C., filtered, and washed the solid with cold dichloromethane. This solid (6.12 g, 18.7 mmoles) was mixed with phosphorous pentachloride (12.9 g, 61.7 mmoles) and the mixture was heated to 110° C. for 4 hours. The mixture was cooled to room temperature and quenched with ice water. Filtered the resulting suspension to give the title compound as a white solid.

Step (c) (L)-2-(7-Bromo-dibenzofuran-2-sulfonylamino)-3-methyl-butyric Acid

When in the procedure of Example 1, (L)-leucine, tert.-butyl ester is replaced with (L)-valine, tert.-butyl ester and dibenzofuran-2-sulfonyl chloride is replaced with 7-bromo-dibenzofuran-2-sulfonyl chloride, the title compound is obtained; melting point=191–193° C.

Example 17

(L)-3-Methyl-2-(7-phenyl-dibenzofuran-2-sulfonylamino)-butyric Acid

Step (a) (L)-2-(7-Bromo-dibenzofuran-2-sulfonylamino)-butyric Acid, tert.-Butyl Ester When in the procedure of Example 1, Step (a), (L)-leucine, tert.-butyl ester is replaced with (L)-valine, tert.-butyl ester and dibenzofuran-2-sulfonyl chloride is replaced with 7-bromo-dibenzofuran-2-sulfonyl chloride, the title compound is obtained.

Step (b) (L)-3-Methyl-2-(7-phenyl-dibenzofuran-2-sulfonylamino)-butyric Acid tert.-Butyl Ester (L)-2-(7-Bromo-dibenzofuran-2-sulfonylamino)-3-methyl-butyric acid, tert.-butyl ester (1.0 g, 2.0 mmoles) and phenyl boronic acid (0.3 g, 2.5 mmoles) were mixed with 10 mL toluene with 5 mL water the 0.5 g sodium carbonate. Tetrakis(triphenylphosphine) palladium (0) (0.15 g, 0.1 mmoles) was added and the resulting mixture was heated to reflux for 6 hours. Another 0.15 g of the palladium catalyst was added and reflux was continued for 16 hours. The reaction was cooled to room temperature and partitioned between 1 M HCl and ethyl acetate. The organic layer was dried over magnesium sulfate and concentrated to give the title compound as a white solid.

Step (c) (L)-3-Methyl-2-(7-phenyl-dibenzoduran-2-sulfonylamino)-butyric Acid (L)-3-Methyl-2-(7-phenyl-dibenzofuran-2-sulfonylamino)-butyric acid, tert.-butyl ester (0.94 g, mmoles) was dissolved in concentrated trifluoroacetic acid and stirred for 2 hours. Concentrated in vacuo and triturated the residue with diethyl ether to give the title compound as an off-white solid; melting point=254–255° C.

INHIBITION STUDIES

Experiments were carried out which demonstrate the efficacy of compounds of Formula I and II as potent inhibitors of stromelysin-1 and gelatinase A. Experiments were carried out with the catalytic domains, i.e., Table 1 shows the activity of the Examples with respect to both stromelysin-1 and gelatinase A, GCD (recombinant gelatinase A catalytic domain); SCD (stromelysin-1 catalytic domain). $IC_{50}$ values were determined using a thiopeptolide substrate, Ac-Pro-Leu-Gly-thioester-Leu-Leu-Gly-OEt (Ye Q.-Z., Johnson L. L., Hupe D. J., and Baragi V., "Purification and Characterization of the Human Stromelysin Catalytic Domain Expressed in *Escherichia coli,*" *Biochemistry*, 1992;31:11231–11235). MMP01, MMP07, MMP09, and MMP13 activity was assayed in a method similar to MMP02 and MMP03 (SCD and GCD). MMP01 and MMP09 can be obtained from Washington University School of Medicine, St. Louis, Mo. MMP07 can be obtained in accordance with the known procedure set forth by Ye Q-Z, Johnson L. L., and Baragi V., "Gene Syntheses and Expression in *E. coli* for PUMP, a Human Matrix Metalloproteinase" *Biochem. and Biophys. Res. Comm.*, 1992;186:143–149. MMP13 can be obtained in accordance with the known procedure set forth by Freije J. M. P., et al., "Molecular Cloning and Expression of Collegenase-3, a Novel Human Matrix Metalloproteinase Produced by Breast Carcinomas" *J. Bio. Chem.*, 1994;269:16766–16773.

Thiopeptolide Assay

Hydrolysis of the thiopeptolide substrate Ac-Pro-Leu-Gly-thioester-Leu-Leu-Gly-OEt (Bachem) is used as the primary screen to determine $IC_{50}$ values for MMP inhibitors. A 100 µL reaction contains 1 mM 5,5'-dithiobis(2-nitrobenzoic acid) (DTNB), 100 µM substrate, 0.1 % Brij, enzyme, and inhibitor in the appropriate reaction buffer. Activated full-length enzymes are assayed at 5 nM, Stromelysin Catalytic Domain (SCD) at 10 nM, and Gelatinase A Catalytic Domain (GaCD) at 1 nM. Inhibitors are screened from 100 µM to 1 nM. Full-length enzymes are assayed in 50 mM HEPES, 10 mM $CaCl_2$, pH 7.0; SCD in 50 mM MES, 10 mM $CaCl_2$, pH 6.0 ; and GaCD in 50 mM MOPS, 10 mM $CaCl_2$, 10 µM $ZnCl_2$, pH 7.0. The change in absorbance at 405 nm is monitored on a ThermoMax microplate reader at room temperature continuously for 20 minutes.

HEPES is 4-(2-hydroxylethyl)piperazine-1-ethane sulfonic acid;

MES is 2-morpholinoethane sulfonic acid menohydrate;

Ac is acetyl;

Pro is proline;

Leu is leucine;

Gly is glycine;

Et is ethyl; and

MOPS is 3-morpholinopropane sulfonic acid.

Soluble Proteoglycan Assay (Stromelysin Natural Substrate Assay) SCD (PG)

Solubilized proteoglycan substrate is prepared from bovine cartilage powder (Sigma) using the method described by Nagase and Woessner in Anal. Biochem. 1980;107:385–392. A 100 μL reaction contains 10 μg/mL proteoglycan, enzyme, and inhibitor in 50 mM MES, 10 mM $CaCl_2$, pH 6.0. Activated full-length stromelysin or stromelysin catalytic domain (SCD) is assayed at 100 nM. Inhibitors are screened from 100 μM to 1 nM. The reaction is incubated at 37° C. for 3 hours then stopped with the addition of 1,10-phenanthroline at a final concentration of 1 mM. Reaction products are separated from undigested substrate using ultrafree-MC polysulfone microcons with a 300,000 molecular weight cut-off membrane (Millipore) and quantified using a modified 1,9-dimethylene blue (DMB) assay described by Farndale, Sayers, and Barrett in *Connective Tissue Research*, 1982;9:247–248. Absorbance is measured at 518 nm using 32 μg/mL DMB in a 1 mL reaction. The standard curve is constructed from 0 to 100 μg shark cartilage chondroitin sulfate C (Sigma).

Gelatin Assay (Gelatinase Natural Substrate Assay (Gel))

Rat tail Type I collagen (Sigma) is denatured by heating at 95° C. for 20 minutes to prepare the gelatin substrate. A 50 μL reaction contains 1.12 mg/mL substrate, enzyme, inhibitor, and 80 μg/mL soy bean trypsin inhibitor as an inert internal standard in 50 mM MOPS, 10 mM $CaCl_2$, 10 μM $ZnCl_2$, pH 7.0. Activated full-length gelatinase A is assayed at 1 nM and gelatinase A catalytic domain (GaCD) at 10 nM. Inhibitors are screened from 100 μM to 1 nM. The reactions are incubated at 37° C. for 30 minutes then stopped with 50 μL at 2×Tricine gel loading buffer (Novex). Reaction products are separated from undigested substrate by electrophoresis on Tricine-SDS 10–20% polyacrylamide gradient gels (Novex). Protein bands are stained with Coomassie Brilliant Blue R and quantified using a Bio Image densitometer (Miliipore). $IC_{50}$ values are calculated from the disappearance of substrate using the sum of the top three bands of each reaction after normalization with the internal standard.

MMP Inhibitor Bioassay

Animals are dosed by gavage with either vehicle or compound at 2, 10, or 50 mg/kg. Blood samples are collected from 3 to 4 animals from each dosing group at 1, 2, 4, 6, and 24 hour postdose, centrifuged, and the plasma immediately frozen at −20° C. Plasma protein is precipitated with an equal volume of acetonitrile and separated by centrifugation at room temperature. The supernate is evaporated to dryness and reconstituted to the original plasma volume with 50 mM Tris, pH 7.6. Ten-fold serial dilutions of the reconstituted plasma samples are prepared in 50 mM Tris, pH 7.6 for dose response assays using the appropriate thiopeptolide assay. The concentration of plasma which yields 50% inhibition of enzyme is determined and used to calculate the inhibitor plasma level from the known $IC_{50}$ value. To demonstrate that the compound can be quantitatively extracted from plasma as active inhibitor, controls for each inhibitor include normal rat plasma, normal rat plasma spiked with compound, and buffer dilutions of compound. All control samples are subjected to acetonitrile precipitation and analyzed with the thiopeptolide assay.

TABLE 1

| Example Number | MMP01 | (GCD) MMP02 | (SCD) MMP03 | MMP07 | MMP09 | MMP13 |
|---|---|---|---|---|---|---|
| 1 | 66 | 0.32 | 1.18 | — | 100 | — |
| 2 | 100 | 2.3 | 1.5 | — | 100 | — |
| 3 | 100 | 0.9 | 0.72 | — | 100 | — |
| 4 | — | 1.7 | 5.4 | — | — | — |

TABLE 1-continued

| Example Number | MMP01 | (GCD) MMP02 | (SCD) MMP03 | MMP07 | MMP09 | MMP13 |
|---|---|---|---|---|---|---|
| 5 | 19 | 0.084 | 0.23 | — | 100 | — |
| 6 | 100 | 0.73 | 4.8 | — | 100 | — |
| 7 | — | 1.2 | 1.0 | — | — | — |
| 8 | — | 9.4 | 14.4 | — | — | — |
| 9 | — | 4.5 | 0.69 | — | — | — |
| 10 | — | 35 | 100 | — | — | — |
| 11 | 1.8 | 0.0045 | 0.015 | 5.0 | — | 0.047 |
| 12 | 32.3 | 0.049 | 0.185 | 10.8 | 100 | 0.34 |
| 13 | — | — | — | — | — | — |
| 14 | 100 | 0.61 | 0.69 | 27 | — | 2.6 |
| 15 | 100 | 100 | 100 | 100 | — | 100 |
| 16 | — | 0.47 | 0.75 | — | — | — |
| 17 | 100 | 0.36 | 0.062 | 6 | — | 0.69 |

TABLE 2

| | Example 5 |
|---|---|
| SCD ($IC_{50}$) | 0.233 μM |
| SCD (PG) ($IC_{50}$) | 8.9 μM |
| GCD ($IC_{50}$) | 0.084 μM |
| Gel ($IC_{50}$) | 0.58 μM |
| Bioassay (50 mg/kg) Peak | 82 μM |
| 24 Hours | 0.18 μM |

What is claimed is:

1. A compound of Formula VII

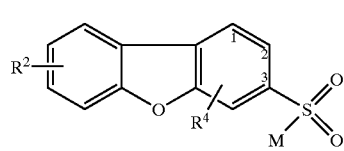

VIII or a pharmaceutically acceptable salt thereof wherein:

$R^2$ and $R^4$ are independently hydrogen, —$C_1$–$C_5$ alkyl, phenyl —$NO_2$, halogen, —$OR^5$, —CN, —$CO_2R^5$, —$SO_3R^5$, —CHO, —$COR^5$, —$CONR^5R^6$, —$(CH_2)_nNR^5R^6$, —$CF_3$, or —$NHCOR^5$, wherein each $R^5$ and $R^6$ are independently hydrogen or $C_1$–$C_5$ alkyl;

M is a natural (L) alpha amino acid derivative having the structure

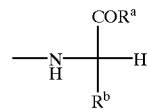

wherein $R^a$ is hydroxy, $C_1$ to $C_6$ straight or branched chain alkoxy, $C_5$ to $C_7$ cycloalkoxy, arylalkoxy, $NH_2$, primary $C_1$ to $C_6$ alkyl amino, secondary $C_1$ to $C_6$ dialkyl amino wherein the alkyl groups are straight or branched chain, secondary amino having a 5- or 6-membered heterocycle which is pyrrolidinyl or piperidinyl, or —$NHOR^5$;

$R^b$ is a side chain of a natural alpha amino acid;

n is 0 to 2; and provided that $R^2$ and $R^4$ are not both H when M is tryptophan.

2. The compound of claim 1 wherein $R^2$ and $R^4$ are hydrogen and M is not tryptophan.

3. The compound of claim 1 wherein $R^a$ is $C_1$–$C_5$ alkoxy or —NHOH or —NHObenzyl.

4. The compound of claim 1 wherein R is the sidechain of the natural alpha amino acid alanine, valine, leucine, isoleucine, cysteine, aspartic acid, phenylalanine, or glycine.

5. The compound of claim 1 wherein the compound is, (L)-2-(dibenzofuran-2-sulfonylamino)-4-methyl-pentanoic acid;

(L)-2-(dibenzofuran-2-sulfonylamino)-3-methyl-pentanoic acid;

(L)-2-(dibenzofuran-2-sulfonylamino)-3-phenyl-propionic acid;

(L)-2-(dibenzofuran-2-sulfonylamino)-propionic acid;

(L)-2-(dibenzofuran-2-sulfonylamino)-3-methyl-butyric acid;

(L)-2-(dibenzofuran-2-sulfonylamino)-acetic acid;

(L)-2-(dibenzofuran-2-sulfonylamino)-succinic acid;

(L)-2-(dibenzofuran-2-sulfonylamino)-3-tritylsulfanyl-propionic acid;

(L)-2-(dibenzofuran-2-sulfonylamino)-3-mercapto-propionic aid;

(L)-2-(dibenzofuran-2-sulfonylamino)-3-methyl-pentanoic acid hydroxyamide;

(L)-2-(dibenzofuran-2-sulfonylamino)-acetic acid tert-butyl ester, (L)-2-(dibenzofuran-2-sulfonylamino)-propionic acid tert-butyl ester;

(L)-2-(dibenzofuran-2-sulfonylamino)-propionic acid tert-butyl ester;

(L)-2-(dibenzofuran-2-sulfonylamino)-4-methyl-pentanoic acid tert-butyl ester;

(L)-2-(dibenzofuran-2-sulfonylamino)-3-methyl-pentanoic acid tert-butyl ester;

(L)-2-(dibenzofuran-2-sulfonylamino)-3-methyl-pentanoic acid benzyloxy-amide;

(L)-2-(dibenzofuran-2-sulfonylamino)-3-phenyl-propionic acid tert-butyl ester;

(L)-2-(dibenzofuran-3-sulfonylamino)-3-methyl-butyric acid;

(L)-2-(dibenzofuran-2-sulfonylamino)-3-methyl-butyric acid;

(L)-2-(5,5-Dioxo-5H-5$\lambda^6$-dibenzothiophene-3-sulfonylamino)-3-methyl-butyric acid;

(L)-2-(Dibenzothiophene-2-sulfonylamino)-3-methyl-butyric acid;

(L)-2-(7-Bromo-dibenzofuran-2-sulfonylamino)-3-methyl-butyric acid;

(L)-3-Methyl-2-(7-phenyl dibenzofuran-2-sulfonylamino)-butyric acid;

3-Methyl-2-(9-methyl-9H-carbazole-3-sulfonylamino)-butyric acid;

2-(9-Benzyl-9H-carbazole-3-sulfonylamino)-3-methyl-butyric acid; or 2-(9H-Carbazole3-sulfonylamino)-3-methyl-butyric acid.

6. A method of treating atherosclerotic plaque rupture, the method comprising administering to a patient having an atherosclerotic plaque at risk for rupture a therapeutically effective amount of a compound of claim 1.

7. A method of treating restenosis following surgical correction of a primary condition, the method comprising administering to a patient having restenosis or at risk of having restenosis a therapeutically effective amount of a compound of claim 1.

8. A method of treating aortic aneurism, the method comprising administering to a patient having aortic aneurism a therapeutically effective mount of a compound of claim 1.

9. A method of treating heart failure, the method comprising administering to a patient having heart failure a therapeutically effective amount of a compound of claim 1.

10. A method of treating periodontal disease, the method comprising administering to a patient having periodontal disease a therapeutically effective amount of a compound of claim 1.

11. A method of treating corneal ulceration, the method comprising administering to a patient having corneal ulceration a therapeutically effective amount of a compound of claim 1.

12. A method of treating burns, the method comprising administering to a patient having burns a therapeutically effective amount of a compound of claim 1.

13. A method of treating decubital ulcers, the method comprising administering to a patient having decubital ulcers a therapeutically effective amount of a compound of claim 1.

14. A method of treating chronic ulcers or wounds, the method comprising administering to a patient having chronic ulcers or wounds a therapeutically effective amount of a compound of claim 1.

15. A method of treating arthritis, the method comprising administering to a patient having arthritis a therapeutically effective amount of a compound of claim 1.

* * * * *